US006827478B2

(12) United States Patent
Becker et al.

(10) Patent No.: US 6,827,478 B2
(45) Date of Patent: Dec. 7, 2004

(54) METHOD AND DEVICE FOR CARRYING OUT THE AUTOMATED PREPARATION AND CHARACTERIZATION OF LIQUID MULTI-CONSTITUENT SYSTEMS

(75) Inventors: Dietmar Becker, Heddesheim (DE); Georg Beck, Böbingen (DE); Stefan Bentz, Lugwigshafen (DE); Wolfgang Best, Freinsheim (DE); Peter Erk, Frankenthal (DE); Günter Etzrodt, Stuttgart (DE); Martin Könemann, Mannheim (DE); Reinhold Rieger, Ludwigshafen (DE); Klaus Unterforsthuber, Dannstadt-Schauernheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 163 days.

(21) Appl. No.: 10/332,843
(22) PCT Filed: Jul. 18, 2001
(86) PCT No.: PCT/EP01/08315
§ 371 (c)(1),
(2), (4) Date: Jan. 14, 2003
(87) PCT Pub. No.: WO02/05939
PCT Pub. Date: Jan. 24, 2002

(65) Prior Publication Data
US 2004/0017728 A1 Jan. 29, 2004

(30) Foreign Application Priority Data
Jul. 18, 2000 (DE) .......................................... 100 34 890

(51) Int. Cl.[7] .......................... B01F 11/00; B01F 15/00; G01J 3/46
(52) U.S. Cl. ....................... 366/108; 366/140; 366/141; 366/605; 356/402
(58) Field of Search ................................ 366/141, 140, 366/108, 605; 356/402

(56) References Cited

U.S. PATENT DOCUMENTS

| | | | | |
|---|---|---|---|---|
| 2,374,430 A | * | 4/1945 | Hexter | 366/141 |
| 3,425,667 A | * | 2/1969 | Berger et al. | 366/140 |
| 3,601,589 A | * | 8/1971 | McCarty | 356/402 |
| 4,212,545 A | * | 7/1980 | Lovasz et al. | 366/177.1 |
| 4,256,131 A | * | 3/1981 | De Remigis | 356/405 |
| 4,272,824 A | * | 6/1981 | Lewinger et al. | 366/141 |
| 4,403,866 A | * | 9/1983 | Falcoff et al. | 366/142 |
| 4,871,262 A | * | 10/1989 | Krauss et al. | 366/605 |
| 5,003,500 A | | 3/1991 | Gerber | 364/526 |
| 5,023,814 A | * | 6/1991 | Guillemin | 382/162 |
| 6,000,837 A | * | 12/1999 | Randsborg et al. | 366/141 |

FOREIGN PATENT DOCUMENTS

| | | |
|---|---|---|
| EP | 316766 | 5/1989 |
| EP | 602737 | 6/1994 |
| EP | 882496 | 12/1998 |
| EP | 907083 | 4/1999 |
| WO | 91/16675 | 10/1991 |

OTHER PUBLICATIONS

Pat. Abst. Japan, 02060800, Mar. 1, 1990.
Jandeleit et al., *Angew. Chem. Int. Ed.*, 1999, vol. 38, pp. 2494–2532.
McFarland et al., *Tibtech*, 1999, vol. 17, pp. 107–115.

* cited by examiner

*Primary Examiner*—Tony G. Soohoo
(74) *Attorney, Agent, or Firm*—Keil & Weinkauf

(57) ABSTRACT

A method of automated preparation and characterization of liquid multicomponent systems comprising at least two, preferably three components comprises the automated preparation of a mixture by combining at least two, preferably three components in a vessel, at least one component being metered in an automated fashion into the vessel, and the automated homogenization of the mixture with subsequent automated measuring and evaluation. The apparatus for conducting this method comprises at least one metering station, one closing station, one homogenizing station, one measuring station for determining formulation properties, and one evaluation unit.

10 Claims, 1 Drawing Sheet

METHOD AND DEVICE FOR CARRYING OUT THE AUTOMATED PREPARATION AND CHARACTERIZATION OF LIQUID MULTI-CONSTITUENT SYSTEMS

BACKGROUND AND SUMMARY OF THE INVENTION

The present invention relates to a method of and apparatus for automatedly preparing and characterizing liquid multicomponent systems comprising at least two, preferably three components.

In the course of the development of liquid formulations, such as dispersions, emulsions or solutions, they are subjected to screening tests in order to optimize them in respect of their action and stability. For this purpose the formulations are first prepared manually and then measured manually. This is a highly complex procedure and hence costly in terms of time and money, especially if the compositions of the formulations are varied at the same time.

It is an object of the present invention to provide a method and apparatus which permit more rapid and reliable screening of liquid multicomponent systems where the composition of the formulation is varied at the same time.

We have found that this object is achieved by a method comprising a plurality of automated steps of preparing and screening the multicomponent systems, and by apparatus having the elements required for this purpose. Although the use of automated methods of discovering new materials, catalysts and active substances has recently been summarized anew—see, for example, B. Jandeleit, D. J. Schäfer, T. S. Powers, H. W. Turner, W. H. Weinberg, Angewandte Chemie Int. Ed. English, 1999, 38, 2494 to 2523 or E. W. McFarland, W. H. and Weinberg, Tibtech, 1999, 17, 107 to 115, the use of automated methods of screening liquid formulations is not known.

The invention accordingly provides a method of automatedly preparing and characterizing at least one liquid multicomponent system comprising at least two, preferably three components, said method comprising at least the following steps:

a) automated preparation of a mixture by combining at least two, preferably three components in a vessel, at least one component being metered into the vessel in an automated fashion;

b) automated homogenization of the mixture obtained in step a) to give the liquid multicomponent system;

c) automated measurement of the liquid multicomponent system; and d) automated evaluation.

The invention additionally provides apparatus for automatedly preparing and characterizing at least one liquid multicomponent system comprising at least two, preferably three components, said apparatus comprising at least the following elements:

(A) a metering station;
(B) a closing station;
(C) a homogenizing station;
(D) a measuring station for determining formulation properties; and
(E) an evaluating unit.

The invention further provides for the use of the method of the invention or apparatus of the invention for the automated preparation and characterization of at least one liquid multicomponent system comprising at least two, preferably three components. Preferred embodiments of the invention are set out in the description, the examples, the FIGURE, and the dependent claims.

DETAILED DESCRIPTION OF THE INVENTION

Figure 1:
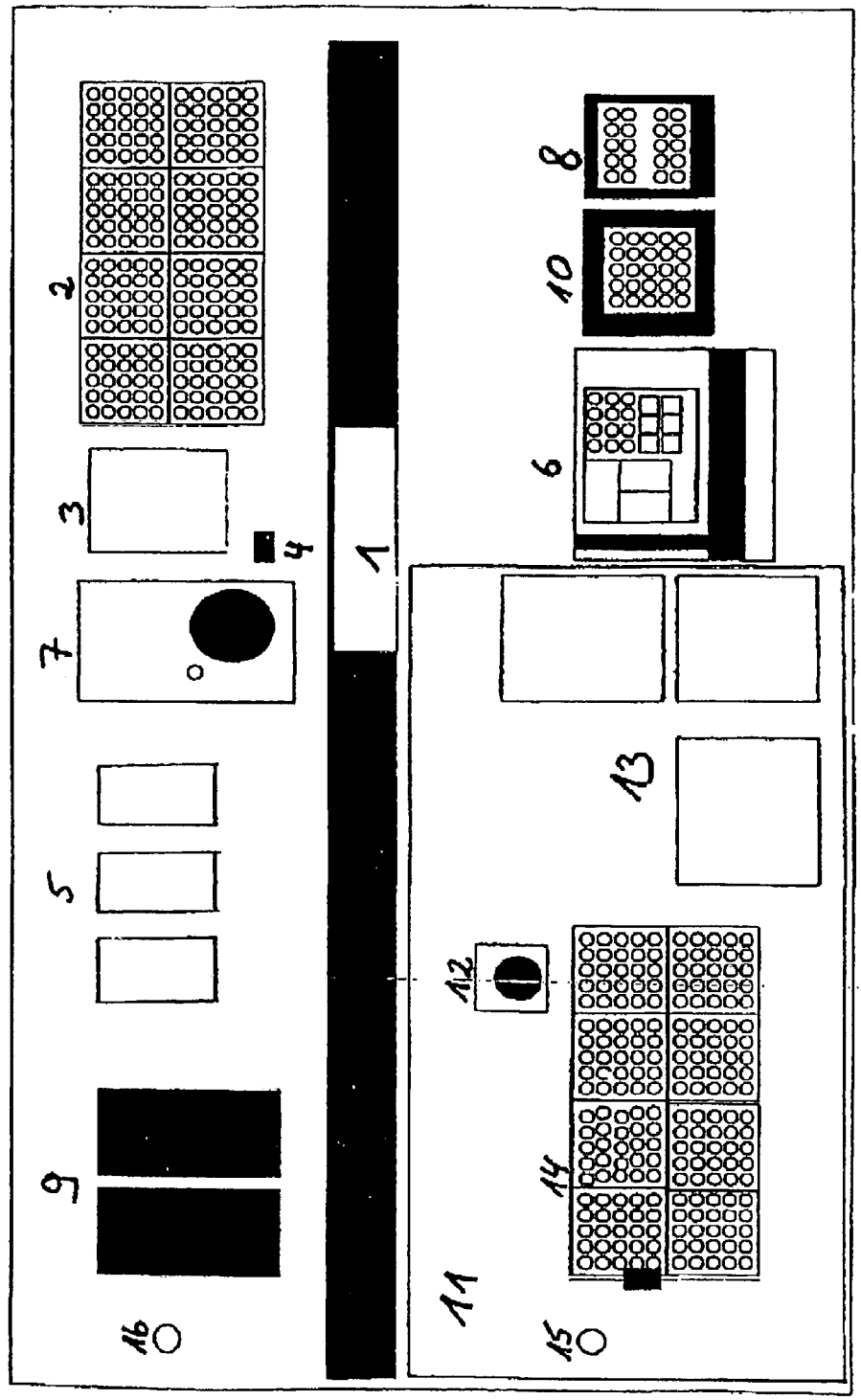
FIG. 1 shows inventively preferred apparatus for automatic screening of liquid multicomponent formulations.

In accordance with the invention, the liquid multicomponent system comprises at least two, preferably three components. The number of components depends on the formulation in question. Advantageously there are from 3 to 10, in particular from 4 to 8, components present, although there may also be more or else, in the case of pigment dispersions, fewer. Said at least three components preferably comprise at least (1) one liquid, at least (2) one solid or liquid substance which is insoluble in the liquid, and at least (3) one surface-active substance. Substance insoluble in the liquid means here that the substance dissolves in the liquid either not at all or at most to an extent of up to 10% by weight. Normally, the multicomponent system is in the form of a dispersion, emulsion, liquid multiphase system, or solution.

In one preferred embodiment of the present invention the multicomponent system is in the form of a dispersion, in particular a pigment dispersion.

In accordance with the state of the art, chromatic pigments in paints are characterized by manual weighed introduction of pigment, base varnish, grinding media, and additives, where appropriate, followed by dispersing of the pigments using a ballmill or a dispersing unit. In order to determine the performance properties of the pigments the pigment dispersions are applied manually, which is very complicated and hence costly in terms of time and money. The transparency of transparent pigments can be assessed by means of non-hiding drawdowns over black/white contrast substrates or by hiding drawdowns of a $TiO_2$ or carbon black blend and rubout.

The color strength and also the transparency, scattering power, hue angle, chroma, lightness, and/or hiding power are likewise determined from the $TiO_2$ blend. Generally speaking, reflection spectra of the manually applied coating films are measured, as described, for instance, in H. G. Völz, Industrielle Farbprüfung [Industrial color testing], VCH Weinheim, 1990.

An optimized coating formulation or pigment formulation has to date been obtained only by means of a large number of time-consuming and costly test runs. It remains unclear, however, whether the optimum ultimately found is an absolute optimum or a local optimum, since systematic and parallel investigation of the sphere of parameters in question is impossible owing to the far-too-large complexity involved.

The paints sector knows of shade elaboration apparatus which is automated for production purposes but in which, rather than pigments being dispersed, pigment-containing pastes are merely mixed, as described, for instance, in R. Huhn, Farbe und Lack, 1999, 9, 102 to 104.

The use of automated methods of discovering new materials, catalysts, and active substances has recently been summarized anew—see, for example, B. Jandeleit, D. J. Schaefer, T. S. Powers, H. W. Turner, W. H. Weinberg, Angewandte Chemie Int. Ed. Engl., 1999, 38, 2494 to 2523 or E. W. McFarland, W. H. Weinberg, Tibtech, 1999, 17, 107 to 115.

There is to date no method which allows the performance properties of the coloristics and rheology of dispersed pigments in fluid media to be detected in an automated fashion.

It is a further object of the present invention, then, to provide a method and apparatus by means of which a multiplicity of dispersions, especially pigment dispersions, preferably simultaneously, can be formulated and characterized in an automated fashion, in particular with the aim of characterizing their coloristics and rheology.

We have found that this object is achieved by the method of the invention, in which the automated preparation of the mixture in step (a) takes place by automated weighed introduction of at least one pigment and at least one varnish into at least one vessel and the automated homogenization in step (b) takes place by automated shaking, to give a pigment dispersion, and the automated measurement in step (c) takes place by colorimetry, the following steps additionally being carried out:

automated closing prior to the automated shaking in step (b), automated opening of said at least one vessel and automated withdrawal of a defined amount of the pigment dispersion prior to the automated measurement in step (c), where appropriate, automated homogeneous mixing of the defined amount of the pigment dispersion with a white/black paste.

We have found, furthermore, that this object is achieved by the apparatus of the invention, in which the measuring station (D) is a colorimeter and the apparatus additionally includes at least the following elements:

a weighing station upstream of the metering station (A),
a dispersing station downstream of the closing station (B),
a withdrawing station, in particular a pipetting station, downstream of the dispersing station,
a further closing station downstream of the withdrawing station.

In one preferred embodiment of the method of preparing a liquid multicomponent system from at least three components, at least (1) one liquid, at least (2) one solid or liquid substance which is insoluble in the liquid, and at least (3) one surface-active substance, the liquid (1) advantageously comprises a solvent, especially water and/or an organic solvent which may be polar or apolar, examples being alcohols such as ethanol and methanol, polyhydric alcohols such as glycerol or polyols, organic solvents such as xylene, toluene, ethyl acetate, tetrahydrofuran, rapeseed oil methyl ester, paraffins and/or hydrocarbon mixtures. Preferred solvents are water or a water/ethanol mixture. The substance (2) insoluble in the liquid comprises, for example, active pharmaceutical substances, active crop protection substances (herbicides, insecticides, fungicides), nutraceuticals, e.g., vitamins, dyes and/or pigments, for paper, hair or leather, for example; organic solvents insoluble in (1), examples being those defined above; synthetic or natural waxes, e.g., beeswax, lanolin; synthetic, vegetable or animal oils, e.g., liquid paraffin, rapeseed oil, soybean oil, pine needle oil, rosemary oil, peanut oil, jojoba oil, coconut oil, almond oil, olive oil, palm oil, castor oil, wheatgerm oil, isopropyl myristate, or essential oils, e.g., dwarf pine oil, lavender oil, rosemary oil, pine needle oil, eucalyptus oil, peppermint oil, sage oil, bergamot oil, terpentine oil, balm oil, juniper oil, lemon oil, aniseed oil, cardamon oil, camphor oil; polymers insoluble in (1), e.g., active substances in cosmetic products (for example, skincare and haircare compositions); specialty chemicals and process chemicals, such as defoamers, water repellents for textile and/or leather, paper sizes, corrosion inhibitors, fuel additives, complexing agents, antioxidants, bleaches, enzymes, stabilizers, e.g., UV stabilizers, biocides, block copolymers and random copolymers. The surface-active substance (3) comprises, for example, solubilizers, surfactants, cosurfactants, hydrotropes, protective colloids such as polyvinylpyrrolidone, generally neutral, cationic, anionic and betainelike dispersants such as polyacrylates, polyacrylic acid and its salts, maleic acid/acrylic acid copolymers, naphthalene-formaldehyde condensates, naphthalenesulfonic acid condensates, phenolsulfonic acid condensates, neutral and cationized starch, polyvinyl alcohol, polyethyleneimine and polyvinylamine, and also modified products thereof, emulsifiers and/or thickeners; especially anionic, nonionic, cationic or amphoteric surfactants, examples being alkyl polyglycosides, fatty alcohol sulfates, fatty alcohol ether sulfates, alkanesulfonates, fatty alcohol ethoxylates, fatty alcohol alkoxylates, fatty alcohol phosphates, fatty alcohol ether sulfonates, alkyl betaines, sorbitan esters, alkoxylated sorbitan esters, sugar fatty acid esters, fatty acid polyglycerol esters, fatty acid partial glycerides, fatty acid carboxylates, fatty alcohol sulfosuccinates, fatty acid sarcosinates, fatty acid isethionates, fatty acid taurinates, citric esters, silicone polymers, silicone copolymers and/or fatty acid polyglycol esters. The precise composition of the multicomponent system is guided by the field of use. Suitable fields of use are specified later on below. A typical dispersion has, for example, the following composition:

| % by weight | Substance | Liquid/solid (melting point) |
| --- | --- | --- |
| 10 to 20 | water-insoluble wax | melting point 40 to 100° C. |
| 69.8 to 89.6 | aqueous protective colloid (1 to 6%) | liquid |
| 0.1 | propionic acid | liquid |
| 0.1 | formaldehyde | liquid |
| 0.1 to 5 | additive X | liquid |
| 0.1 to 5 | additive Y | solid |

The solution of the protective colloid here contains from 1 to 6% by weight of protective colloid, the remainder being water. The additives X and Y may comprise emulsifiers or dispersants. Another typical formulation has the following composition: 30% by weight synthetic or vegetable oil, e.g., isopropyl myristate; from 0.1 to 5% by weight emulsifier X; from 0.1 to 5% by weight emulsifer Y; and water as the remainder. Emulsifiers X and Y comprise customary emulsifiers.

Step (a) of the method of the invention comprises automated preparation of a mixture by the combining of at least two, preferably at least three components in a vessel, at least one component being metered in an automated fashion into the vessel. The vessel appropriately comprises a glass or small bottle with a screw or snap-on closure, preferably with a volume of 1 to 50 ml. There is no restriction here on the way in which the components are combined, provided it can be automated. The components may be combined by introducing one or more components initially, especially one component; automatic metering of one or more components; and/or automatic withdrawal, especially pipetting, of one or more components from one or more stock containers. In one preferred embodiment of the invention, in step (a) the vessel is empty and at least one component is metered or pipetted in a defined amount, in an automated fashion, from a stock container into the empty vessel.

In another particularly preferred embodiment, the components are combined in the vessel by means of at least one suitable robot. It is also possible for metering, pipetting and/or dilution steps to be carried out simultaneously in parallel for a plurality of samples.

In the preferred embodiment of the method of the invention for preparing pigment dispersions, the automated preparation of the mixture in step (a) takes place by automated weighed introduction of at least one pigment and at least one varnish into at least one vessel.

The varnish is preferably a solventborne varnish, such as a CAB varnish or an alkyd-melamine varnish, for example, or a waterborne varnish.

Preferably, different pigments are weighed simultaneously, together with said at least one varnish, into different vessels which together form a grid.

In another preferred procedure, said at least one pigment is weighed together with different varnishes into different vessels which together form a grid.

In a further preferred embodiment of the method of preparing pigment dispersions, said at least one pigment formulation is weighed in different metered additions, together with said at least one varnish, into different vessels which together form a grid. With particular preference, the weighed introduction of the pigment formulations, the unpigmented varnishes, and the grinding media is carried out by means of at least one suitable robot.

Step (b) comprises automated homogenization of the mixture obtained in step (a), to give the liquid multicomponent system. The homogenization procedure is not subject to any restriction, provided an automated implementation is possible. Preferably, homogenization takes place by means of Ultraturrax, ultrasonic dispersing and/or shaking. Where shaking is carried out, the vessel sealed in an automated fashion prior to shaking, whereas in the case of ultrasonic dispersion or Ultraturrax the vessel is sealed in an automated fashion afterward. Sealing is preferably carried out by means of an appropriate robot. Advantageously, the homogenizing time can be set and changed in an automatically controllable manner. Depending on the homogenization technique, it is also possible to homogenize a plurality of samples in parallel.

In a further advantageous embodiment of the invention, after step (b) and before step (c), or after step (a) and before step (b), the liquid multicomponent system is heated and/or cooled in an automated fashion, and if desired may be at the same time mixed, by shaking, for example. In this case, judiciously, the heating or cooling time is settable and controllable automatically. It is also possible to heat and/or cool a plurality of samples in parallel. Heating and/or cooling of the multicomponent system to a certain temperature over a defined period of time allows storage tests to be conducted.

In the preferred embodiment of the method of the invention for preparing pigment dispersions, the automated homogenization in step (b) takes place by automated shaking to give a pigment dispersion. Prior to the automated shaking in step (b), said at least one vessel is closed in an automated fashion.

Said at least one vessel is preferably closed by means of a robot.

Further, preferably, the closed vessel is placed by the robot, for automated shaking, into a dispersing apparatus, preferably a dispersing unit, with particular preference a Skandex disperser.

Preferably, the dispersing time can be set and changed in an automatically controllable manner. Depending on the dispersing time, dispersions having different particle size distribution and hence also different properties are produced, including in particular different coloristic properties.

After step (b) has been carried out it is possible to determine the colloidal stability of the pigment dispersion by way of its rheology.

In step (c), the liquid multicomponent system is subjected to automated measuring. Where the measurement method requires it, the vessel is opened in an automated fashion before step (c) and, if necessary, sealed again after the end of the measurement, something which in each case may be carried out by means of a robot. The measuring operation preferably takes place by means of measurement methods for the automated determination of formulation properties, such as stability, viscosity, homogeneity, phase behavior, particle size and particle size distribution, overall concentration, solids content, foam behavior, cloud point, concentrations of components, coagulum content, stability to hard water, and/or chemical properties, such as the determination of functional groups of the components. With particular preference, measurement takes place by means of automated viscosity measurements, transmission and reflectance measurements, particle size measurements, acoustic techniques such as techniques, for example, for determining particle sizes or the air content, spectroscopic techniques such as Raman, NIR and/or IR spectrometry, and/or image analysis for homogeneity testing. Most preferably, the measuring takes place by means of at least one measuring technique selected from automated viscosity measurement, particle size measurement, transmission and/or reflectance measurement, and/or image analysis for homogeneity testing. One investigation or a plurality of investigations in succession may be carried out. If required, the vessels are opened or sealed between the individual measurements. If required, the measurement systems, e.g., the rotational element of the rheometer, are automatically cleaned. The viscosity measurement may be conducted with any viscometer, such as a rotational viscometer, for example. The homogeneity is determined by way of an image analysis with different lightness levels. In order to determine bodying, sedimentation or concentration gradients of formulations, e.g., emulsions or dispersions, use is made of transmission or reflectance measurements by means of laser beam, which are carried out at different points in the vertical extent of the sample vessel. To determine the turbidity of a solution or microemulsion, transmission or reflectance is likewise measured. The particle size determination is carried out by means of light diffraction or light scattering. In one preferred embodiment, measurement comprises bringing the multicomponent system to the measurement site by means of a robot. Where necessary for a measuring technique, a sample of the multicomponent system is removed in an automated fashion from the vessel beforehand, preferably by means of pipetting. Appropriately, the instrument or measuring station used for the measurement is of modular construction, thereby permitting the different measuring techniques to be exchanged depending on the measurement task.

In the embodiment of the method of the invention for preparing pigment dispersions, automated opening of said at least one vessel takes place prior to the automated measurement in step (c).

The automated opening is preferably likewise performed by means of a robot.

It is followed by automated withdrawal of a defined amount of the pigment dispersion.

Preferably, a suitable robot is used here as well, and withdraws the desired amount of pigment dispersion by means of a withdrawing unit, preferably a syringe. In order to avoid blockage of the entrance of the syringe when the color paste or pigment dispersion is being drawn up, it is preferred to insert a disposable syringe to a distance of only 2 to 4 mm in each case, the depth of insertion preferably being ensured by means of an ultrasonic measurement of the distance.

Preferably, the color paste thus withdrawn is also weighed at the same time by means of an appropriate balance.

The automated measurement in step (c) takes place, in the method of preparing pigment dispersions, by colorimetry.

Colorimetry is preferably performed by recording at least one reflection spectrum, the measurement of the reflection spectrum taking place preferably from a distance of 0.1 to 5 cm directly on the liquid pigment dispersion.

In step (d), the results obtained in step (c) are evaluated. Appropriately, this is done by means of appropriate software, and, if desired, the measurement is terminated as soon as at least one measurement method characterizes the liquid multicomponent system as being unsuitable. The evaluation may also comprise documentation of the composition of the formulation, and documentation of the preparation sequence and the measurement results.

In the embodiment of the method of the invention for preparing pigment dispersions, in which the measuring takes place by colorimetry, preferably by recording at least one reflection spectrum, the reflection spectrum recorded is evaluated by means of appropriate colorimetry software, preferably determining, inter alia, at least one of the following colorimetric parameters:

dH (δ hue angle), dL (δ lightness), dC (δ chroma), ddE (δ transparency), FAE (color strength/color equivalent).

These parameters allow conclusions to be drawn about the colloidal stability, the size of the particles in dispersion, and the dispersibility.

Preference is given to determining the color equivalent FAE to a comparative sample, and the dispersibility.

The colorimetric values of the comparative sample are preferably likewise determined by means of the described method of the invention.

In one preferred embodiment of the method of the invention for preparing pigment dispersions, the automated withdrawal of a defined amount of the pigment dispersion prior to measurement in step (c) is followed by automated homogeneous mixing of the defined amount of the pigment dispersion with a white/black paste. Homogenization with the white/black paste may take place preferably in two different ways.

In one preferred embodiment of the method of the invention for preparing pigment dispersions, a defined white/black paste is discharged to a vessel, the color paste or the defined amount of pigment dispersion is metered in from the syringe, and a homogeneous paste is produced by shaking.

In another preferred embodiment, both the color paste or the defined amount of pigment dispersion and the white/black paste are drawn up in defined amounts in disposable syringes and the two syringes are connected with a hose which has a bulge section. By back-and-forth movement of the syringe bulbs, the pastes are homogenized; the effect of the syringe bulbs is that the paste which is on the inner walls of the syringe is completely homogenized. The black/white paste contains from 2 to 40% of $TiO_2$ or carbon black.

In another preferred embodiment of the method of the invention for preparing pigment dispersions, in step (a), i.e. during the automated weighing of said at least one pigment and said at least one varnish into at least one vessel, one or more grinding media are weighed in at the same time.

As grinding media it is preferred to use, for example, small glass beads, SAZ beads or steel beads. These grinding media produce performance-relevant dispersing more effectively and more quickly, since they represent a considerable input of mechanical energy into the system.

Furthermore, in another preferred embodiment of the method of the invention for preparing pigment dispersions, the automated weighing of said at least one pigment and said at least one varnish into said at least one vessel is accompanied by the weighed introduction of at least one or more additives as well. By means of these additives it is possible to stabilize the colloidal pigment particles in said at least one varnish: for example, by the maintenance of a steric distance or by way of corresponding electrical charging.

Possible additives include all surface-active substances, among them surfactants, polymers, and pigment derivatives. They act as defoamers, deaerators, wetting agents, dispersants and/or as leveling additives and/or as rheology modifiers.

The invention additionally provides apparatus as defined above. Suitable metering stations include dosimats, hose pumps and/or metering stations for melts having a temperature of up to 300° C. The metered amount may be controlled or checked by way of a balance. A particularly suitable closing station is a screw station with lid dispenser. The homogenizing station preferably comprises an Ultraturrax, an ultrasonic disperser, a shaker/agitator or a mixer. A combination of two or more of these devices is also possible. The measuring station preferably comprises instruments suitable for determining the abovementioned formulation properties, an example being colloidal properties of the formulations. Examples of typical measuring stations are rheometers, turbidity measuring instruments, measuring instruments for determining transmission and/or reflectance, instruments for image analysis, Raman spectrometers, NIR spectrometers, IR spectrometers and/or particle size measuring instruments. It is also possible to use two or more of said instruments. Particular preference is given to an instrument for determining rheology properties, an instrument for measuring transmission and/or reflectance, an instrument for particle size measurement, and/or an instrument for image analysis for homogeneity testing.

In one preferred embodiment of the invention, the apparatus further comprises at least one of the following elements:

(A') a pipetting station;

(C') a heating and/or cooling station, with or without mixer and/or shaker; and (F) a robot.

One further preferred embodiment of the apparatus of the invention provides apparatus for automatedly preparing and characterizing at least one dispersion, in particular at least one pigment dispersion, the measuring station (D) being a colorimeter and the apparatus additionally including at least the following elements:

a weighing station upstream of the metering station (A), a dispersing station downstream of the closing station (B), a withdrawing station, in particular a pipetting station, downstream of the dispersing station, a further closing station downstream of the withdrawing station.

The apparatus of the invention for preparing and characterizing pigment dispersions preferably further includes at least one of the following elements:

a metering station for grinding media, a metering station for solid and/or liquid additives, a robot, a metering station for white/black pastes.

The individual elements and/or instruments are preferably arranged in the following way:

In a weighing station, preferably for pulverulent pigments, and a downstream metering station for grinding media, defined mixtures of grinding media and pulverulent pigments are produced. In a downstream metering station for solid and/or liquid additives it is possible to add desired additives. In a downstream metering station, preferably for unpigmented base varnishes, a corresponding base varnish is added.

In a downstream closing station, preferably a screwing station, the vessel containing the mixture is closed, preferably by means of an appropriate robot, and is supplied, again preferably by means of a robot, to a dispersing unit, preferably a Skandex disperser. In the dispersing unit, a pigment dispersion is produced by shaking. Preferably it is possible here for a plurality of vessels, containing different mixtures and together forming a grid, to be shaken in parallel at the same time, so producing different pigment dispersions simultaneously.

After a variable dispersing time, which can be set, the vessels containing the grinding media and the pigment dispersions are removed from the dispersing unit, preferably by means of a robot, and are opened in a suitable withdrawing station. In a corresponding withdrawing station, in particular a pipetting station, a defined amount of the pigment dispersion is withdrawn from each vessel. In order to prevent grinding media blocking the entry to the syringe while the pigment dispersion is being drawn up, a disposable syringe is inserted only to a distance of 2 to 4 mm into the millbase. The depth of insertion is ensured by means of an ultrasonic measurement of the distance. The pigment dispersion withdrawn in the pipetting station in this way is preferably weighed and, in a further preferred embodiment of the invention, is mixed homogeneously with a defined amount of white paste in order to produce pigment dispersions.

The homogenized pastes are preferably placed in a glass dish by means of a robot and the hiding layers of the pastes are measured by means of an appropriate colorimeter. Light having a wavelength of from 400 to 700 nm is shone in as flashes of light, at an angle of 45°, each at intervals of 20 nm. The measurement spot has a diameter of approximately 3 cm.

By mixing with white paste and black paste there become in virtually any layered hiding formulation of the transparent pigment pastes. In this way it is possible to determine the transparency.

A reflection spectrum is measured directly on the liquid paste from a distance of from 0.1 to 5 cm. Evaluation is carried out by means of appropriate colorimetry software, in order to determine the colorimetric parameters dH, dL, dC, ddE, the color equivalent FAE to a comparative sample, and the dispersibility.

In a further preferred embodiment, the evaluating unit (E) comprises at least one computer for data capture and data evaluation. It is also possible to provide a documenting unit.

Preferably, the individual elements and/or instruments of the apparatus of the invention for automated preparation and characterization of at least one liquid multicomponent system comprising at least two, preferably at least three components are arranged, and the method of the invention for preparing said liquid multicomponent system is carried out, in the manner shown in FIG. 1, which shows preferred apparatus for automatic screening.

As shown in FIG. 1, preferably a robot (1), which is preferably positioned on a rail, first withdraws small bottles from a store (2), which are then labeled by the labeler (3) so that they can be identified by a barcode reader (4). These small bottles may already contain one or more components or may be empty; preferably they are empty. Advantageously, they have not been sealed. It is then possible by way of a plurality of metering stations (5), for example, by way of three metering stations as shown in FIG. 1, to meter into the bottles polymer melts, hot melts, e.g., hot wax; highly viscous substances; solids such as powders or granules, for example; liquids such as oils, water, surfactants, solutions—of active substances and auxiliaries, for example—alcohols and/or organic solvents, for example. The receivers and metering units may be heated. It is also possible to withdraw one or more components from a stock vessel (not shown) by way of a pipetting station (6) and to pipette them into the bottle. After the components have been combined, the bottle containing the sample may, if required, be sealed in a closing station (7), especially a screwing station with lid dispenser. If required, the bottles may be heated in the heating station (8) prior to homogenizing. From said station (8), the bottle is brought by the robot (1) to the homogenizing units (9). After the homogenizing the bottles, if still open, are sealed in the closing station (7). Thereafter, the bottle with the sample may pass to the heating station (8) or to a cooling station (10), preferably with integrated horizontal shaker and fan, or to both stations in succession. From there, or if no heating or cooling operations are carried out, the robot (1) transfers the bottle with the sample to the screening or measuring station (11). In this station the bottles, if necessary, are opened at the screwing station (12) and measured by means of one or more of the abovementioned measuring instruments. FIG. 1 depicts 3 measuring instruments (13) symbolically, of which one or more may be employed. The screening station (11) also includes storage space (14) for samples. The samples may therefore be measured repeatedly at particular time intervals. The samples may also be removed from the entire unit shown in FIG. 1 and replaced in the unit at any desired later point in time, at store (2) and/or storage space (14) or at the cooling station (10) and/or the heating station (8), for subsequent renewed treatment/investigation. For this purpose, the samples may be unambiguously identified by way of their barcode. After the results have been evaluated, the samples may be sorted in accordance with quality features, with the possibility of poor samples being discarded as waste (15) in the screening station (11) or else outside of that station: for example, discarded as waste (16) as early as after homogenization. Throughout the sequence, the bottle is brought to the desired position by the robot (1) in each case. The possibility also exists of bringing the samples to the desired point within the screening station (11) independently of the robot (1), for example, with the aid of a further robot. By this means, samples may be measured and prepared in parallel independently of one another. Following this sequence, the samples thus prepared and measured may be stored outside the screening station (11), for example, in the heating station (8), before being subsequently measured again. The samples may also be pipetted into different vessels, already containing solutions or solvents, e.g., water (pipetting taking place by way of pipetting station (6)). The "daughter" samples thus prepared may then again be homogenized and/or heated, if required, and subsequently measured in the screening station (11).

The present invention further embraces the use of the method of the invention and apparatus of the invention for automatedly preparing and characterizing at least one liquid multicomponent system comprising at least two, preferably three components.

In one preferred embodiment of the present invention, the present invention embraces the use of the method of the invention and apparatus of the invention for automatedly formulating and automatedly characterizing at least one pigment, in particular for simultaneously automatedly formulating and automatedly characterizing a plurality of pigment formulations.

The invention is especially suitable for developing new liquid multicomponent systems, especially size dispersions and defoamer emulsions for papermaking; in the laundry detergent industry for the screening of hydrotropes (solubilizers) for the production of readily soluble laundry detergent tablets/compacts and highly concentrated liquid formulations, and also acid or alkaline cleaners which dissolve to give clear, homogeneous solutions; and also for the development of microemulsions; for the development of cosmetic formulations such as creams, lotions, shampoos, hair conditioners, shaving lotions, and deodorant formulations, for example; for liquid vitamin formulations, food formulations, active substance formulations in crop protection and pharmacy; for the development of water repellent emulsions, for leather or textile, for example; for the development of solvent-based or water-based paints and coatings; and for the development of inkjet inks. Generally speaking, the invention is suitable for the development of colloidal and disperse formulations and also of solutions or liquid multiphase systems. The invention is further suitable for the development of additives and auxiliaries for formulations, including, for example, for developing new surfactants and specialty surfactants intended, for example, for the abovementioned formulations.

The present invention makes it possible to prepare and characterize a large number of liquid formulations in a short time. By means of an intelligent software program, the screening of a plurality of samples may be optimized in terms of time, by conducting steps (a) to (c) in parallel on different samples. In other words, while, for example, a measurement is being carried out on sample 1, sample 2 is homogenized in the meantime, while the formulation components are simultaneously metered into the vessel of sample 3. The software also makes it possible not to continue investigating the sample that was originally to be investigated with a plurality of measuring instruments as soon as a measured value characterizes the sample as being unsuitable. Therefore, if a sample which should, for example, be homogeneous is characterized by the image analysis system as being inhomogeneous, it is possible not to carry out any further measurement on this sample, e.g., no subsequent viscosity measurement. As a result, sample screening is made shorter. Using the invention it is possible, for example, to investigate rapidly the behavior of new additives and commercially customary surfactants and emulsifiers or auxiliaries in liquid formulations while at the same time varying the composition of the formulation and so to optimize liquid formulations efficiently and reliably. Whereas, with the procedure customary to date, one person could prepare and investigate from 10 to 20 formulations a day, it is possible by means of the invention for one person to prepare and characterize at least 100 samples a day, with the possibility of storage of formulations at the same time. This is a forceful demonstration of the economy and utility of the present invention.

A preferred embodiment of the present invention, the provision of a method and apparatus for preparing and characterizing pigment dispersions, makes it possible simultaneously to formulate a plurality of different dispersions and to characterize them immediately thereafter without a large time delay. Applying the different pigment dispersions to appropriate carrier materials is no longer necessary: instead, the performance properties, especially those of the coloristics and rheology, may be detected directly in the fluid media containing the dispersed pigments, in an automated fashion. In this context it is possible to use solvents, oils or waxes alongside the conventional, unpigmented aqueous and solventborne varnish systems.

Whereas with the at least partly manual procedure which has been the norm to date for the formulation and characterization of pigment dispersions it has been possible to investigate only about 10 pigment dispersions per day, it is possible by means of the present invention to analyze from about 90 to 100 pigment dispersions per day.

The invention is illustrated by means of the following examples, which represent preferred embodiments but do not restrict the invention. The examples show a typical procedure when screening emulsions (example 3) and dispersions (example 1) and also crop protection formulations (example 2) and a solubilizate (example 4).

EXAMPLE 1

Screening of Dispersions

A bottle with a capacity of 10 or 50 ml is taken from the store and labeled and the barcode is read. Subsequently, highly mobile or viscous surfactants and/or dispersants and/or organic solutions are metered in. Then, in the sequence indicated, protective colloids are metered in at 70° C., water is metered in at 70° C., and wax melt is metered in at 80° C. After heating for 5 minutes, dispersion is carried out in an ultrasound unit with a 1–12 mm sonotrode for from 1 to 10 minutes. The sonotrode is cleaned under hot water and with ultrasound. Thereafter, the bottle has a lid screwed onto it and the sample is cooled to room temperature on the shaker table for from 15 to 30 minutes. The samples are subsequently transferred to the screening station, in which they are determined for homogeneity, by means of an image analysis instrument, and viscosity. The samples are subsequently stored. All of the operations are carried out in an automated fashion.

EXAMPLE 2

Screening of Crop Protection Formulations

A bottle with a capacity of 10 ml is taken from the store by a robot. The barcode is applied adhesively by the automatic labeler and the barcode is subsequently read. Then 3 ml of water and 3 ml of oleic acid methyl ester containing a herbicide dissolved to a concentration of 25% by weight are metered in in succession at the metering stations. Subsequently, at the pipetting station, two liquid surfactants are pipetted in, in each case from 0.1 to 1.0 g. The bottle is then sealed with a screw lid and the contents are homogenized by a shaker. Thereafter the bottle is transferred to the screening station. After 1 hour, the sample is checked for homogeneity by means of image analysis. If the sample is homogeneous and displays neither separation/sedimentation tendencies nor bodying tendencies, this sample A is screwed open and together with a new vessel for sample B, containing 30 g of water, is conveyed by the robot to the automatic pipetting unit. In the latter unit, 0.6 g of sample A is withdrawn and pipetted into the vessel of sample B. When this vessel is sealed, the contents (sample B) are shaken, and the vessel and contents are transferred to the screening station by the robot. In the screening station, the aqueous dilute sample B is investigated for homogeneity by means of transmission measurement, at time intervals which are defined in the method sequence. Homogeneous and inhomogeneous samples B are sorted in the sample rack of the screening station according to specified time-based stability criteria. Optionally, the samples B which are inhomogeneous on a time basis may also be discarded, so producing space for further samples if required. All operations are carried out in an automated fashion. In this way, different active substances and/or auxiliaries may be screened rapidly and efficiently.

EXAMPLE 3
Screening of Emulsions

A bottle with a capacity of 50 ml is taken from the store and labeled and the barcode is read. Then oils are metered in and emulsifiers/surfactants are metered in. The sample is homogenized with the mixer. Then water and, if desired, further surfactants are metered in. The sample is sealed, the mixture is heated to 80° C., the bottle is opened, and the contents are dispersed in an ultrasound device having a 1–12 mm sonotrode for from 1 to 10 min. The bottle is then screwed shut and the sample is cooled on the shaker table and then transferred to the screening station. There, homogeneity and viscosity are determined. Subsequently, the sample is stored in the heating station at 60° C. for 2 hours and again transferred to the screening station for the measurements. The inhomogeneous samples are subsequently discarded and the stable samples are stored further. All operations are carried out in an automated fashion.

EXAMPLE 4
Screening of Solubilizates

A bottle with a capacity of 50 ml is taken from the store and labeled and the barcode is read. Then oils are metered in and solubilizers are added by pipette. The sample is homogenized with the mixer. It is then heated to 80° C. and water heated to 70° C. is mixed in. The mixture is homogenized with the mixer, cooled on the shaker table and then transferred to the screening station. There, the homogeneity and turbidity of the sample are measured. All operations are carried out in an automated fashion, the bottle being opened and closed, respectively, in an automated fashion at the corresponding points. By this means, different solubilizates can be screened rapidly.

EXAMPLE 5
Preparation and Characterization of Pigment Dispersions

A 100 ml glass bottle is provided with a bar code. Then 1.5 g of a pulverulent pigment preparation, 20 g of glass beads (diameter: 3 mm) and 15 g of an unpigmented varnish are weighed in. A plurality of bottles filled in this way are dispersed simultaneously in the dispersing unit. After 15 minutes of dispersing, the bottles are taken from the dispersing unit and processed further individually. One bottle is first of all unscrewed. Using a 20 ml disposable syringe, 1.5 g of the color pigment dispersion are weighed together with 2.0 g of a 20% $TiO_2$ dispersion into a 20 ml bottle. The contents of the sealed 20 ml bottle are homogenized by shaking. Following homogenization (3 minutes) the contents of this bottle are poured into a petri dish and a reflection spectrum of the dispersion is recorded. The 100 ml bottles are sealed again and dispersed for another 2 hours. The mixing of the color pigment dispersion with the $TiO_2$ dispersion is repeated and again a reflection spectrum is recorded. All operations are carried out in an automated fashion.

We claim:

1. A method of automatedly preparing and characterizing at least one pigment dispersion comprising at least two components, said method comprising at least the following steps:

(a) automated preparation of a mixture by automated weighed introduction of at least one pigment and at least one varnish into at least one vessel;

(b) automated homogenization of the mixture obtained in step (a) by automated shaking to give the pigment dispersion;

(c) automated evaluation by colorimetric measurement of the pigment dispersion, and the following steps being carried out in addition:

automated closing before the automated shaking in step (b), automated opening of said at least one vessel and automated withdrawal of a defined amount of the pigment dispersion prior to the automated measurement in step (c), where appropriate, automated homogeneous mixing of the defined amount of the pigment dispersion with a white/black paste.

2. A method as claimed in claim 1, wherein one or more grinding media are weighed in in step (a).

3. A method as claimed in claim 1, wherein one or more additives are weighed in in step (a).

4. A method as claimed in claim 1, wherein the colorimetric measurement in step (c) takes place by recording at least one reflection spectrum or recording with a CCD camera.

5. A method as claimed in claim 1, wherein in step (a) the vessel is empty and at least one component is metered or pipetted in a defined amount, automatedly, from a stock container into the vessel.

6. A method as claimed in claim 1, wherein the evaluation in step (c) takes place by means of appropriate software.

7. A method as claimed in claim 1, wherein after step (b) and before step (c) the liquid multicomponent system is heated and/or cooled in an automated fashion, with or without simultaneous mixing.

8. Apparatus for automatedly preparing and characterizing at least one pigment dispersion comprising at least two components, said apparatus comprising at least the following elements:

(A) a metering station (5);

(B) a closing station (7);

(C) a homogenizing station (9);

(D) a colorimeter (11), and (E) an evaluating unit, said apparatus further comprising at least the following elements:

a weighing station upstream of the metering station (A), a dispersing station downstream of the closing station (B), a withdrawing station, in particular a pipetting station, downstream of the dispersing station, a further closing station (7) downstream of the withdrawing station, and the automation is carried out by means of a robot.

9. Apparatus as claimed in claim 8, further comprising at least one of the following elements:

a metering station for grinding media, a metering station for solid and/or liquid additives, a robot, a metering station for white/black pastes.

10. Apparatus as claimed in claim 8, wherein the evaluating unit (E) comprises at least one computer for data capture and data evaluation.

* * * * *